US007263467B2

(12) United States Patent
Sackellares et al.

(10) Patent No.: US 7,263,467 B2
(45) Date of Patent: Aug. 28, 2007

(54) MULTI-DIMENSIONAL MULTI-PARAMETER TIME SERIES PROCESSING FOR SEIZURE WARNING AND PREDICTION

(75) Inventors: James Chris Sackellares, Gainesville, FL (US); Leonidas D. Iasemidis, Scottsdale, AZ (US); Deng-Shan Shiau, Gainesville, FL (US); Linda Dance, Gainesville, FL (US); Panos M. Pardalos, Gainesville, FL (US); Wanpracha A. Chaovalitwongse, Hillsborough, NJ (US)

(73) Assignees: University of Florida Research Foundation Inc., Gainesville, FL (US); Arizona Board of Regents, Tempe, AZ (US)

( * ) Notice: Subject to any disclaimer, the term of this patent is extended or adjusted under 35 U.S.C. 154(b) by 588 days.

(21) Appl. No.: 10/673,329

(22) Filed: Sep. 30, 2003

(65) Prior Publication Data
US 2004/0127810 A1    Jul. 1, 2004

Related U.S. Application Data

(60) Provisional application No. 60/414,364, filed on Sep. 30, 2002.

(51) Int. Cl.
*G06F 15/00* (2006.01)
(52) U.S. Cl. .................................... 702/183; 702/190
(58) Field of Classification Search ............. 702/66, 702/67, 70, 73, 179, 181, 182, 183, 184, 702/185, 189, 190; 600/544, 545, 547
See application file for complete search history.

(56) References Cited

U.S. PATENT DOCUMENTS

| | | | |
|---|---|---|---|
| 5,857,978 A | 1/1999 | Hively et al. | |
| 5,995,868 A | 11/1999 | Dorfmeister et al. | |
| 6,061,593 A | 5/2000 | Fischell et al. | |
| 6,304,775 B1 | 10/2001 | Iasemidis et al. | |
| 6,484,132 B1 * | 11/2002 | Hively et al. | ............... 702/190 |
| 6,507,754 B2 | 1/2003 | Le Van Quyen et al. | |
| 2003/0065535 A1 * | 4/2003 | Karlov et al. | .................. 705/2 |

OTHER PUBLICATIONS

Iasemidis et al., "Phase Space Topography of the Electrocorticogram and the Lyapunov Exponent in Partial Seizures," Brain Topography, vol. 2, No. 3, pp. 187-201 (1990).
Pincus, "Approximate Entropy as a Measure of System Complexity," Proceedings of the National Academy of Science of the United States of America, vol. 88, pp. 2297-2301 (1991).

(Continued)

*Primary Examiner*—Edward Raymond
*Assistant Examiner*—Mohamed Charioui
(74) *Attorney, Agent, or Firm*—Woodcock Washburn LLP

(57) ABSTRACT

Characterizing the behavior of a chaotic, multi-dimensional system is achieved by measuring each of a number of signals associated with the system, and generating therefrom, a spatio-temporal response based on each signal. Multiple dynamical profiles are then generated for each spatio-temporal response, where each of the multiple dynamical profiles correspond to a different one of multiple dynamical parameters. Over a period of time, a determination is made as to whether a certain level of dynamic entrainment and/or disentrainment exists between the dynamical profiles associated with a selected one or a selected combination of dynamical parameters. Seizure warnings and/or predictions are provided based on this determination.

5 Claims, 11 Drawing Sheets

OTHER PUBLICATIONS

J.C. Sackellares et al., "Epileptic Seizures as Neural Resetting Mechanisms," Epilepsia, vol. 38, Suppl. 3, p. 189, (1997).

L. D. Iasemidis et al., "Dynamical Resetting of Human Brain at Epileptic Seizures: Application of Nonlinear Dynamics and Global Optimization Techniques," IEEE Transactions on Biomedical Engineering, vol. 51, No. 3, pp. 493-506, (2004).

Wolf et al., "Determining Lyapunov Exponents from a Time Series," Physica D., vol. 16D, pp. 285-317, (1985).

Eckmann et al. "Lyapunov Exponents from Time Series," Physical Review A, vol. 34, pp. 4971-4972 (1986).

Iasemidis et al., "Adaptive Epileptic Seizure Prediction System," IEEE Transactions in Biomedical Engineering, vol. 50, No. 5, pp. 616-627, (2003).

Iasemidis et al., "Prediction of Human Epileptic Seizures Based on Optimization and Phase Changes of Brain Electrical Activity," Optimization Methods and Software, vol. 18, No. 1, pp. 81-104, (2003).

Iasemidis et al., "Seizure Warning Algorithm Based on Spatiotemporal Dynamics of Intracranial EEG," Mathematical Programming, vol. 101, No. 2, pp. 365-385, (2004).

* cited by examiner

US 7,263,467 B2

MULTI-DIMENSIONAL MULTI-PARAMETER TIME SERIES PROCESSING FOR SEIZURE WARNING AND PREDICTION

RELATED PATENTS

This patent application relates to commonly assigned U.S. Pat. No. 6,304,775, which issued on Oct. 16, 2001. It is incorporated herein by reference in its entirety. This application also claims priority from U.S. Provisional Application No. 60/414,364 filed in the U.S. Patent and Trademark Office on 30 Sep. 2002.

STATEMENT REGARDING FEDERALLY SPONSORED RESEARCH AND DEVELOPMENT

The research and development effort associated with the subject matter of this patent application was supported by the Department of Veterans Affairs and by the National Institute of Biomedical Imaging and Bioengineering of the National Institutes of Health (NIBIB/NIH) under grant no. 8R01EB002089-03.

FIELD OF INVENTION

The present invention involves the field of signal processing. More particularly, the present invention involves the multi-parameter processing of time series signals associated with multi-dimensional systems, such as the electrical and/or electromagnetic signals generated by the brain.

BACKGROUND

A multi-dimensional system exhibits behavior autonomously or as a function of multiple variables in response to a system input. A chaotic system is one that exhibits chaotic behavior (i.e., behavior characterized by random responses to an inexperienced observer) during normal operation. The brain is an example of a multi-dimensional system that also exhibits chaotic behavior during normal operation. However, in a relatively significant percentage of the human population, the brain experiences deterministic, abnormal episodes characterized by less chaotic behavior. This abnormal behavior may be caused by a wide variety of conditions. Epilepsy is one of these conditions.

Epilepsy is a chronic disorder characterized by recurrent brain dysfunction caused by paroxysmal electrical discharges in the cerebral cortex. At any given time, Epilepsy affects approximately 50 million people worldwide. If untreated, an individual afflicted with epilepsy is likely to experience repeated seizures, which typically involve some level of impaired consciousness. Some forms of epilepsy can be successfully treated through medical therapy. However, medical therapy is less effective with other forms of epilepsy, including Temporal Lobe Epilepsy (TLE) and Frontal Lobe Epilepsy (FLE). With TLE and FLE, removing the portion of the hippocampus and/or cerebral cortex responsible for initiating the paroxysmal electrical discharges, known as the epileptogenic focus, is sometimes performed in an effort to control the seizures.

For quite some time, the medical community has attempted to develop techniques that provide seizure prediction and/or seizure warning, where it will be understood that seizure prediction is a long-range forecast of seizure-onset time, whereas seizure warning is a long-range indication that conditions conducive to an impending seizure presently exist. Any such technique would certainly have numerous clinical and non-clinical application. For example, in order to more effectively treat certain Epilepsy patients, such a technique might be used in conjunction with a device, perhaps an implanted device, that delivers a dosage of anti-seizure medication into the patient's bloodstream for the purpose of averting an impending seizure.

In another example, such a technique might be used during a pre-surgical evaluation to assist in pinpointing the epileptogenic focus. It is understood that during a seizure, blood flow to the epileptogenic focus significantly increases. If certain radio-labeled ligands are injected into the patient's bloodstream in a timely manner, it is possible to monitor that increase using radiography, thereby allowing a surgeon to accurately pinpoint the boundaries of the epileptogenic focus, which the surgeon will remove during the surgery. A true seizure prediction and/or warning technique would provide an indication of an impending seizure well in advance, therefore providing sufficient time to prepare for and administer, for example, the aforementioned radiography ligand.

One of the most important tools for evaluating the physiological state of the brain is the electroencephalogram (EEG). The standard for analyzing and interpreting an EEG is visual inspection of the graphic tracing of the EEG by a trained clinical electroencephalographer. However, there is no established method for predicting seizure onset or for providing a seizure warning well before seizure onset by visually analyzing an EEG. Moreover, the use of traditional signal processing techniques on EEG signals has likewise yielded little practical information. These traditional techniques are limited in their effectiveness because the brain is a multi-dimensional system that produces nonlinear signals in space and time. Thus, traditional signal processing techniques employing standard, linear, time series analysis methods cannot detect the spatio-temporal properties that are critical in providing effective seizure warning and prediction.

U.S. Pat. No. 6,304,775, however, describes systems and methods capable of effectively generating true seizure warnings and predictions well in advance of impending seizures. The systems and methods described in this patent take advantage of the spatio-temporal characteristics exhibited by certain sites within the brain, when compared with the spatio-temporal characteristics exhibited by other sites within the brain, as these characteristics are noticeably different prior to an impending seizure as compared to the spatio-temporal characteristics exhibited by these same sites during seizure free intervals. In fact, these spatio-temporal characteristics may be noticeable hours, and in some cases, days before the occurrence of a seizure. As such, the systems and methods described in U.S. Pat. No. 6,304,775 use these differences as a seizure transition indicator.

More particularly, U.S. Pat. No. 6,304,775 describes, among other things, a technique that provides timely impending seizure warning (ISW), seizure susceptibility period detection (SSPD) and time to impending seizure prediction (TISP). The technique involves acquiring electrical or electromagnetic signals generated by the brain, where each signal corresponds to a single EEG electrode or channel. Each signal is pre-processed (e.g., amplified, filtered, digitized) and sampled. This results in a sequence of digital samples for each signal over a period of time, referred to therein as an epoch. The samples are then used to generate a phase-space portrait for each signal epoch.

For each phase-space portrait, a parameter reflecting rate of divergence is computed based on adjacent trajectories in the phase space, where rate of divergence, in turn, is one parameter that reflects the chaoticity level of the corresponding signal. In U.S. Pat. No. 6,304,775, the parameter used is the short-term, largest Lyapunov exponent ($STL_{MAX}$).

In general, the $STL_{MAX}$ values associated with each EEG signal (i.e., each EEG channel) are compared to the $STL_{MAX}$ values associated with each of the other channels. The comparisons are preferably achieved by applying a T-statistic, which results in a sequence of statistical values, or T-index values, for each channel pair, where a sequence of T-index values represents a level of correlation or entrainment between the spatio-temporal response associated with the two channels that make up each channel pair.

The technique, when first employed, goes through an initialization period. During this initialization period, a number of "critical" channel pairs is identified, where U.S. Pat. No. 6,304,775 generally defines a critical channel pair as a pair of channels that exhibits a relatively high level of entrainment (i.e., relatively low T-index values for a pre-defined period of time) prior to seizure onset.

During the initialization period, a patient may experience one or more seizures. After each, the list of critical channel pairs is updated. Eventually, the list of critical channel pairs is considered sufficiently refined, and the initialization period is terminated. Thereafter, the ISW, SSPD and TISP functions may be activated and the T-index values associated with the critical channel pairs are monitored and employed in generating timely ISWs, SSPDs and/or TISPs.

Co-pending U.S. patent application Ser. No. 10/648,354 describes both methods and systems that optimize the critical channel selection process. Optimization is achieved in several ways. First, the selection is achieved more efficiently as it is based on a limited amount of statistical data (e.g., T-index data) within a pre-defined time window preceding, and in some instances, following seizure-related events. Critical channel selection is further optimized by selecting and reselecting critical channels for each of a number of predictors, where a predictor is a given number of critical channel groups "x", a given number of channels per group "y", and a given total number of channels "N."

SUMMARY OF THE INVENTION

The present invention focuses on generating signals that more effectively reflect the non-linear dynamical characteristics of a multi-dimensional system, such as the brain. In U.S. Pat. No. 6,304,775, chaoticity profiles based, for example, on $STL_{MAX}$ are generated from corresponding time-series signals, where each profile reflects the chaoticity or rate of divergence of a corresponding channel. However, other parameters may also provide a good basis for measuring the dynamical characteristics of a system such as the brain. Thus, in accordance with preferred embodiments of the present invention, multiple dynamical parameters are considered. In general, for each of a number of channels, multiple dynamical profiles are generated, where each is based on a different one of multiple corresponding dynamical parameters. Several statistical measures are then generated for each of at least one channel group over the course of an initialization period, where each statistical measure reflects a level of correlation among the channels that make up the channel group, and where each statistical measure is derived as a function of corresponding dynamical profiles associated with at least one or more dynamical parameters. The statistical measures are, at the end of the initialization period, used to select one or a combination of dynamical parameters, where the resulting statistical measure associated with the selected one or combination of dynamical parameters provides the most effective indication of impending seizures as compared to the statistical measures associated with other dynamical parameters or other combinations thereof. Subsequent to the initialization period, the statistical measure associated with the selected one or combination of dynamical parameters is continuously derived and employed for purpose of issuing an ISW, SSPD and/or TISP.

Accordingly, it is an objective of the present invention to provide an ISW, SSPD and/or TISP well in advance of seizure onset, based on multiple dynamical parameters.

It is another objective of the present invention to provide an ISW, SSPD and/or TISP well in advance of seizure onset, based on a selected one or a selected combination of dynamical parameters.

It is still another objective of the present invention to utilize the ISW, SSPD and TISP features of the present invention in conjunction with various in-patient applications, including pre-surgical evaluation and diagnosis procedures.

In accordance with a first aspect of the present invention, the above-identified and other objects are achieved through a method of analyzing a multi-dimensional system. The method involves generating a multi-dimensional signal for each of a plurality of channels associated with the multi-dimensional system, and generating multiple dynamical profiles for each channel based on the corresponding multi-dimensional signal, where each profile reflects the dynamical characteristics of the corresponding channel in accordance with one of multiple dynamical parameters. For a group of channels, a number of statistical measures are then generated, where each of the statistical measures reflects a correlation level between corresponding dynamical profiles, and where each of the corresponding dynamical profiles is associated with one of the multiple dynamical parameters. The method next involves selecting at least one dynamical parameter from amongst the multiple dynamical parameters. Thereafter, a statistical measure for the channel group is generated, where the statistical measure reflects a correlation level between corresponding dynamical profiles associated with the selected at least one dynamical parameter. The behavior of the multi-dimensional system is then characterized as a function of the statistical measure, generated for the channel group, that reflects the correlation level between corresponding dynamical profiles associated with the selected at least one dynamical parameter.

In accordance with a second aspect of the present invention, the above-identified and other objects are achieved through a method and a system of analyzing the brain. This method and system involve acquiring a plurality of signals, where each signal represents a corresponding channel associated with a different spatial location of the brain. A state-space representation is then generated for each channel as a function of a corresponding one of the acquired signals. This method and system also involve generating a plurality of dynamical profiles from each state-space representation, where each of the plurality of dynamical profiles generated from a given state-space representation reflects the dynamical characteristics of the state-space representation in accordance with a corresponding one of multiple dynamical parameters. For each of one or more channel groups, a plurality of statistical profiles are generated, where each of the plurality of statistical profiles associated with a given channel group reflects a correlation level amongst corresponding dynamical profiles associated with at least one of the multiple dynamical parameters. At least one dynamical parameter is then selected from amongst the multiple dynamical parameters, and thereafter, a statistical profile is generated for each of one or more channel groups, where the statistical profile reflects a correlation level for the dynamical profiles associated with the selected at least one dynamical parameter. The state dynamics of the brain is then characterized as a function of the statistical profile, generated for each of the one or more channel groups, which reflects the correlation level of the dynamical profiles associated with the selected at least one dynamical parameter.

BRIEF DESCRIPTION OF THE FIGURES

The objects and advantages of the present invention will be understood by reading the following detailed description in conjunction with the drawings in which:

FIG. 10 illustrates an on-line system that incorporates the ISW, SSPD and TISP features of the present invention.

DETAILED DESCRIPTION OF THE INVENTION

Figure 1:
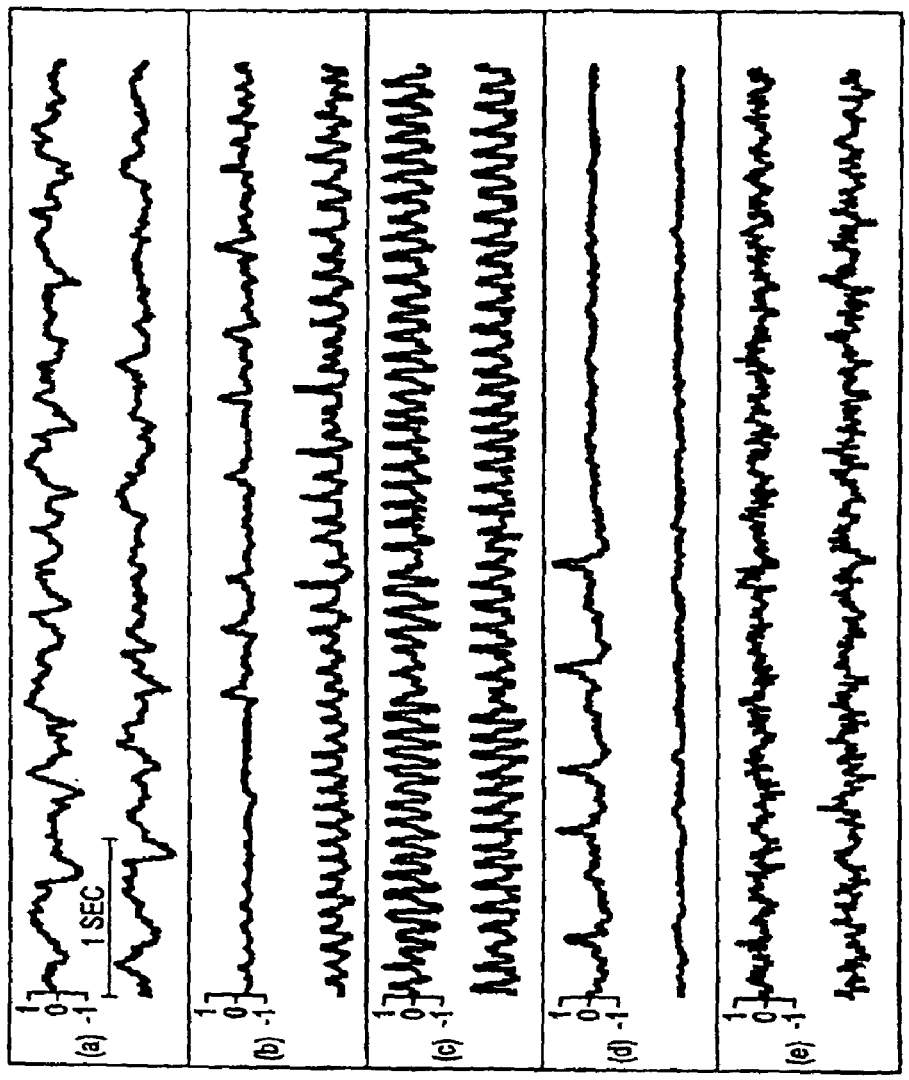
FIGS. 1(a)-(e) illustrates an exemplary, single channel EEG signal as a patient transitions through the various stages of an epileptic seizure.

Seizures, including epileptic seizures, are multiple stage events. The various stages include a preictal stage, an ictal stage, a postictal stage and an interictal stage. FIGS. 1(a-e) illustrate an exemplary electroencephalogram (EEG) signal, recorded from an electrode overlying an epileptogenic focus, as a patient transitions through the various stages of an epileptic seizure. More specifically, FIG. 1(a) illustrates a time sequence of the EEG signal during the preictal stage, which represents the period of time preceding seizure onset. FIG. 1(b) illustrates a time sequence of the EEG signal during the transition period between the preictal stage and the ictal stage, which include seizure onset. It follows that FIG. 1(c) then reflects the EEG signal during the ictal stage, that is within the epileptic seizure, where the ictal stage begins at seizure onset and lasts until the seizure ends. FIG. 1(d), like FIG. 1(b), covers a transitional period. In this case, FIG. 1(d) illustrates a time sequence of the EEG signal during the transition from the ictal stage to the postictal stage, and includes the seizure's end. FIG. 1(e) then illustrates the EEG signal during the postictal stage, where the postictal stage covers the time period immediately following the end of the seizure.

As stated, the preictal stage represents a period of time preceding seizure onset. More importantly, the preictal stage represents a time period during which the brain undergoes a dynamic transition from a state of spatio-temporal chaos to a state of spatial order and reduced temporal chaos. Although it will be explained in greater detail below, this dynamic transition during the preictal stage is characterized by the dynamic entrainment of the spatio-temporal responses associated with various cortical sites. As set forth in U.S. Pat. No. 6,304,775 and co-pending U.S. patent application Ser. No. 10/648,354, the dynamic entrainment of the spatio-temporal responses can be further characterized by:

(1) the progressive convergence (i.e., entrainment) of the maximum Lyapunov exponent values (i.e., $L_{MAX}$) corresponding to each of the various, aforementioned cortical sites, where $L_{MAX}$ provides a measure of chaoticity associated with the spatio-temporal response of a corresponding cortical site; and (2) the progressive phase locking (i.e., phase entrainment) of the $L_{MAX}$ profiles associated with the various cortical sites.

The dynamic entrainment of the spatio-temporal responses may also be characterized by the convergence and/or phase-locking of profiles generated based on dynamical parameters other then $L_{MAX}$. Thus, in a preferred embodiment of the present invention, other parameters (i.e., other dynamical parameters) are taken into consideration, and they include the rate of change in angular frequency $\Omega_{MAX}$, approximate entropy ApEn, Pattern-match ApEn, Pesin's Identity $h_\mu$, and the Lyapunov Dimension $d_L$. Each of these chaoticity parameters will be described in greater detail below.

As one skilled in the art will readily appreciate, an EEG signal, such as any of the EEG signals depicted in FIGS. 1(a-e), is a time series signal that represents a temporal response associated with the spatio-temporal interactions of a particular portion of the brain where the corresponding electrode happens to be located. Since, the brain is a complex, multi-dimensional system, EEG signals and other known equivalents do not and cannot visibly reflect the true spatio-temporal characteristics exhibited by the brain. Thus, traditional linear and nonlinear methods of processing EEG signals for the purpose of providing seizure prediction and/or warning have proven to be generally ineffective as the critical spatio-temporal characteristics exhibited by the brain during the preictal stage cannot be detected from EEG signals alone. Yet, these critical spatio-temporal characteristics exist long before seizure onset, in some cases, days before seizure onset. As such, these spatio-temporal characteristics exhibited by the brain during the preictal stage are essential to any true seizure prediction scheme.

Figure 2:
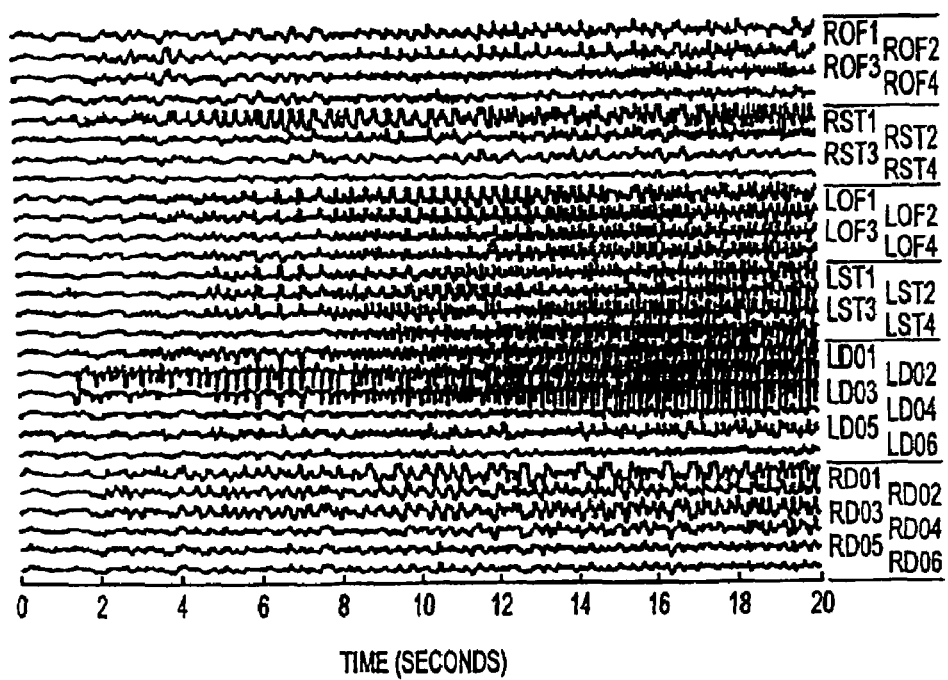
FIG. 2 illustrates a typical, continuous multi-channel EEG segment prior to and during seizure onset.

To better illustrate the deficiency of EEG signals, FIG. 2 shows a 20 second EEG segment covering the onset of a left temporal lobe seizure. The EEG segment of FIG. 2 was recorded from 12 bilaterally placed hippocampal depth electrodes (i.e., electrodes LTD1-LTD6 and RTD1-RTD6), 8 subdural temporal electrodes (i.e., electrodes RST1-RST4 and LST1-LST4), and 8 subdural orbitofrontal electrodes (i.e., electrodes ROF1-ROF4 and LOF1-LOF4). Seizure onset begins approximately 1.5 seconds into the EEG segment as a series of high amplitude, sharp and slow wave complexes in the left depth electrodes, particularly in LTD1-LTD3, though most prominently in LTD2. Within a matter of seconds, the seizure spreads to right subdural temporal electrode RST1, and then to the right depth electrodes RTD1-RTD3. Of particular importance is the fact that the EEG signals appear normal prior to seizure onset approximately 1.5 seconds into the EEG segment.

The present invention provides an early ISW based on the aforementioned spatio-temporal changes that occur during the preictal stage. The present invention provides this capability even though EEG signals do not manifest any indication of an impending seizure during the preictal stage, as illustrated in FIG. 2. In addition to providing an ISW, the present invention is also capable of providing a seizure susceptibility period detection (SSPD), that is, the presence of abnormal brain activity long before the occurrence of a seizure, for example, during an interictal period days before a seizure. Furthermore, the present invention is capable of providing a time to impending seizure prediction (TISP), wherein the TISP reflects an amount of time that is expected to elapse before seizure onset.

Figure 3:
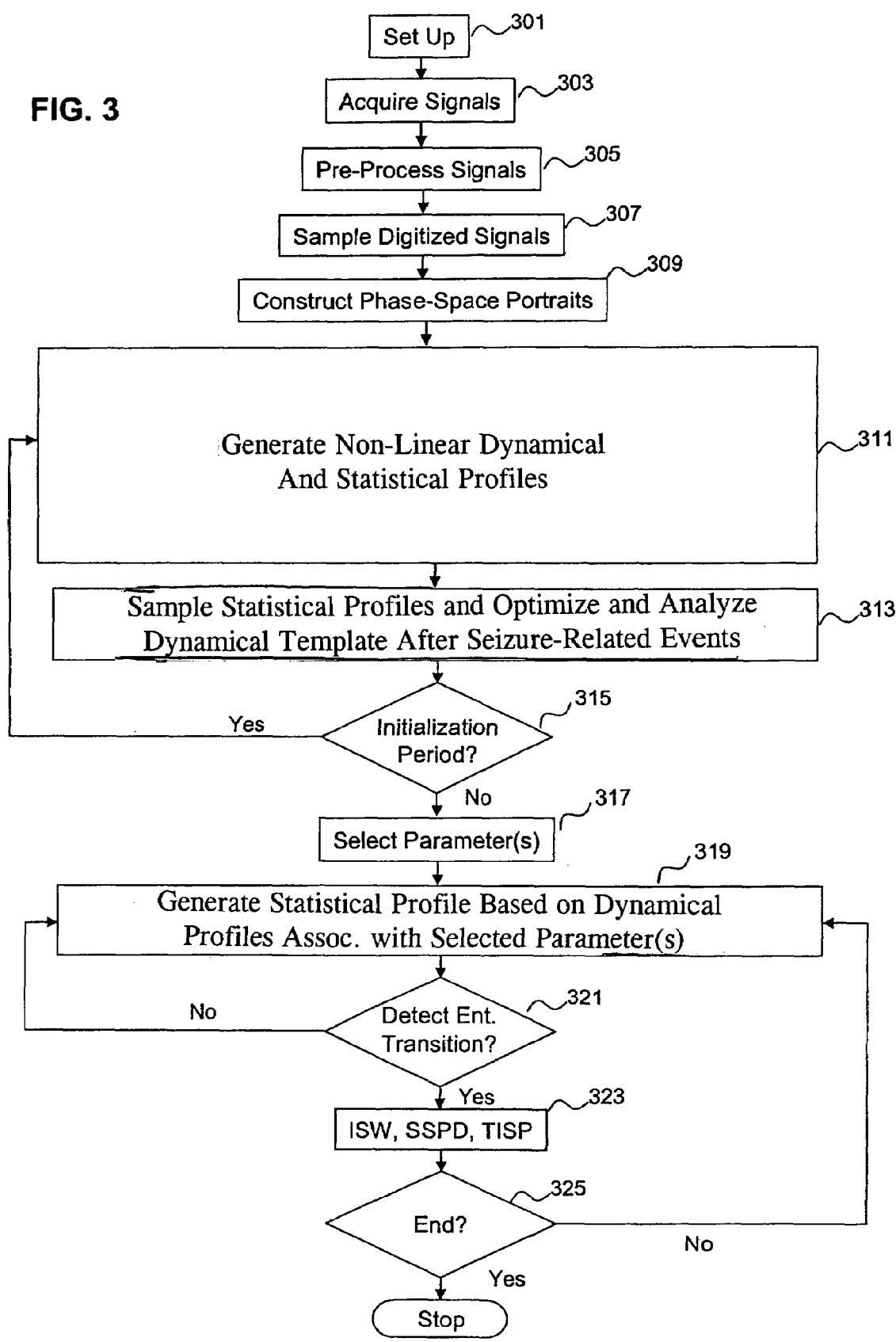
FIG. 3 is a flowchart depicting techniques for providing early ISW, SSPD and TISP in accordance with exemplary embodiments of the present invention.

FIG. 3 is a flowchart depicting an exemplary embodiment of the present invention. In general, the method illustrated by the flowchart of FIG. 3 involves selecting one dynamical parameter or a combination of dynamical parameters from amongst multiple dynamical parameters at the end of an initialization period. Thereafter, an ISW, SSPD and/or TISP are issued based on a statistical measure associated with at least one channel group.

It should be noted that in accordance with a preferred embodiment of the present invention, the methods illustrated in FIGS. 3A and 3B are employed in conjunction with a computer-based system, where the methods are implemented in software, firmware or a combination of both. For ease of discussion, the methods are generally referred to herein as the "algorithm."

Turning now to the individual steps associated with the method of FIG. 3, step 301 represents a setup procedure. During the setup procedure, the operator of the computer-based system, such as a physician or clinician, selects or defines various parameters, parameter values and threshold levels used by the algorithm during execution. For example, it is at this point that the operator may be given the option of selecting, from a list of possible choices, the multiple dynamical parameters that are to be used by the algorithm to ultimately determine the behavior of the system under test (e.g., the brain). Similarly, the operator may be given the option of selecting the statistical test that the algorithm will use to determine the correlation level of the channels that make up one or more channel groups. In a preferred embodiment, the statistical test that is used is the nonparametric randomized block ANOVA (Analysis of Variance) test, or $X^2$-statistic, where the values produced as a result of applying an $X^2$-statistic are referred to herein as $X^2$-index values.

Still further, the operator may, during setup step 301, define the value of various thresholds. One such threshold is referred to herein as the disentrainment threshold $X^2_D$, where $X^2_D$ represents a $X^2$-index value threshold, and where a corresponding channel group is considered significantly and statistically disentrained when the $X^2$-index profile associated therewith exceeds this threshold. Another threshold is referred to herein as the entrainment threshold $X^2_E$, where $X^2_E$ represents a $X^2$-index value threshold, below which a corresponding channel group is considered sufficiently and statistically entrained.

In accordance with step 303, the algorithm begins acquiring electrical or electromagnetic signals generated by the brain. In a preferred embodiment, each signal corresponds with a single EEG channel. Each signal is pre-processed, per step 305, where pre-processing typically includes signal amplification, filtering and digitization. Each digitized signal is then sampled, as shown in step 307, and based on each sampled signal, a corresponding sequence of phase-space portraits are generated from each signal, as shown by step 309, where each phase-space portrait is based on samples falling within in a corresponding time window called an epoch.

In step 311, the algorithm first generates a number of dynamical data sequences or dynamical profiles for each channel. The dynamical profiles associated with a given channel are generated as a function of a phase-space portrait associated with that channel, where each of the dynamical profiles reflects the non-linear dynamical characteristics of the spatio-temporal response for that channel in accordance with a corresponding one of the multiple dynamical parameters. In FIG. 3, six exemplary dynamical parameters are shown: $STL_{MAX}$, $\Omega_{MAX}$, ApEn, PM-ApEn, $h_i$ and $d_L$. However, it will be understood that parameters other than or in addition to those shown in FIG. 3 may be employed.

In a preferred embodiment of the present invention, each of the dynamical profiles generated during step 311, for a given channel, may actually reflect an average dynamical measurement, where the average dynamical measurement may be derived, for example, by averaging a sequence of dynamical data values falling within overlapping or non-overlapping "sliding" time windows. Further in accordance with a preferred embodiment of the present invention, the dynamical profiles associated with each dynamical parameter, for each channel, are generated by the algorithm using parallel processing techniques that are well known to those of skill in art.

Further in accordance with step 311, the algorithm generates several statistical measures for each of at least one channel group. As stated previously, the algorithm may do so by applying a nonparameteric randomized block ANOVA test. For a given channel group, the statistical measures are a function of the dynamical profiles, associated with each of the channels that make up the channel group, corresponding to one or a combination of the multiple dynamical parameters.

It will be understood that the nonparameteric randomized block ANOVA test is exemplary, where the statistical profiles generated as a result of applying this test comprise a sequence of $X^2$-index values, and where each sequence of $X^2$-index values are referred to herein as an $X^2$-index profile. Accordingly, the algorithm may be set up so that it applies other statistical tests for testing the difference among channels with multiple parameter inputs.

In step 313, a limited sample of values (e.g., a sample falling within one or more predefined time windows) from each $X^2$-index profile associated with the at least one channel group is obtained following each of several seizure-related events. A seizure-related event may be an actual seizure or what is called an entrainment transition (i.e., an event characterized by a relatively high level of correlation amongst one or more channel pairs as indicated by relatively low $X^2$-index values). The time window may, for example, be a 10 or 20-minute time window preceding or mostly preceding the seizure-related event.

A seizure may be detected using any of a number of techniques. For example, a seizure may be detected by an attending clinician, who does so by physically observing the behavior of the patient. Alternatively, a seizure may be detected by the algorithm itself; for example, by detecting a rapid decrease in the values associated with one or more $X^2$-index profiles, followed by a rapid increase in the one or more $X^2$-index profiles. As stated in U.S. Pat. No. 6,304,775, a seizure may also be detected by observing certain EEG signal manifestations indicative of a seizure. Other methods of seizure detection may be employed.

If a seizure is detected, the algorithm will, in accordance with a preferred embodiment of the present invention, mark the occurrence of the seizure, for example, by setting a status flag and storing the time associated with seizure onset in memory. The algorithm may set the status flag and store seizure onset time automatically after it detects the seizure or in response to an action taken by the clinician. It is the setting of the status flag that causes the algorithm to sample the several $X^2$-index profiles generated for each of the at least one channel groups, as indicated in step 313.

An entrainment transition event, on the other hand, may be detected if and when the algorithm determines that the value associated with one or more $X^2$-index profiles has dropped below a predefined entrainment threshold $X^2_E$. In an alternative embodiment, the $X^2$-index profiles would have to first exceed the $X^2_D$, prior to falling below the entrainment threshold $X^2_E$ to constitute an entrainment transition event.

When the method illustrated in FIG. 3 is first employed, for instance, when it is used in conjunction with a new patient, there is an initialization period. The primary purpose of the initialization period is to provide a period of time during which the algorithm optimizes a dynamical template, where the dynamical template reflects each of the several $X^2$-index profiles generated for the at least one channel group, as sampled over a number of seizure-related events during the transition period, as indicated by step 313, and the "YES" path out of decision step 315. More specifically, the dynamical template provides an indication and/or quantification of the sensitivity level associated with each $X^2$-index profile with respect to impending seizure prediction during the various transitional states (e.g., interictal, preictal, ictal and post-ictal states). As one skilled in the art will readily appreciate, the dynamical template may quantify the sensitivity level in terms of a number of true seizure predictions per a total number of seizure-related events during the initialization period and/or a number of false predictions per a the total number of seizure-related events. Moreover, one skilled in the art will understand that those $X^2$-index profiles that exhibit a relatively high number of true predictions versus false predictions are likely to exhibit relatively low $X^2$-index values just prior to or during the seizure-related events.

At the end of the initialization period, as indicated by the "NO" path out of decision step 315, and step 317, the algorithm selects one of or a combination of dynamical parameters, from amongst the other parameters, where the selected one or combination of dynamical parameters corresponds with the one $X^2$-index profile that, during the intitializatin period, exhibited the best sensitivity level (i.e., provided the best indication of impending seizures) compared to the other $X^2$-index profiles generated for the at least one channel group.

After the initialization period and the selection of one or a combination of dynamical parameters, it will be understood that the algorithm continues to acquire, pre-process, digitize and construct phase-space portraits as shown in steps 303 through 309. Per step 319, the algorithm then begins generating dynamical profiles based on the selected at least one or combination of dynamical parameters, for each channel. From these dynamical profiles, the algorithm generates a corresponding $X^2$-index profile for at least one channel group.

In addition to generating an $X^2$-index profile for each of at least one channel group, based on corresponding dynamical profiles associated with the selected one or combination of dynamical parameters, the algorithm monitors each $X^2$-index profile. In accordance with decision step 321, the algorithm determines whether the conditions are indicative of an entrainment transition. The algorithm may do so, as explained above, by determining whether the $X^2$-index values associated with the $X^2$-index profile for one or more channel groups have dropped below the entrainment threshold $X^2_E$, or alternatively, exceeded the disentrainment threshold $X^2_D$ prior to dropping below the entrainment threshold $X^2_E$. If the algorithm determines the conditions do not indicate an entrainment transition, in accordance with the "NO" path out of decision step 321, the algorithm continues to generate the dynamical profiles based on the selected one or combination of dynamical parameters, and it continues to generate a corresponding $X^2$-index profile for each of at least one channel group. If, however, the algorithm determines the conditions reflect an entrainment transition, in accordance with the "YES" path out of decision step 321, the algorithm will issue an ISW, SSPD and/or TISP, per step 323. A more detailed discussion of the ISW, SSPD and TISP is provided below.

Certain steps associated with the method illustrated in FIG. 3 will now be described in greater detail. For example, step 303 involves acquiring electrical or electromagnetic signals generated by the brain. In accordance with a preferred embodiment of the present invention, electrodes are used to record electrical potentials, where each electrode corresponds to a separate channel, and where recordings are made using differential amplifiers. In referential recordings, one of the electrodes is common to all channels. The electrodes are strategically placed so that the signal associated with each channel is derived from a particular anatomical site in the brain. Electrode placement may include, for example, surface locations, wherein an electrode is placed directly on a patient's scalp. Alternatively, subdural electrode arrays and/or depth electrodes are sometimes employed when it is necessary to obtain signals from intracranial locations. One skilled in the art will appreciate; however, that the specific placement of the electrodes will depend upon the patient, as well as the application for which the signals are being recorded.

Figure 4A:
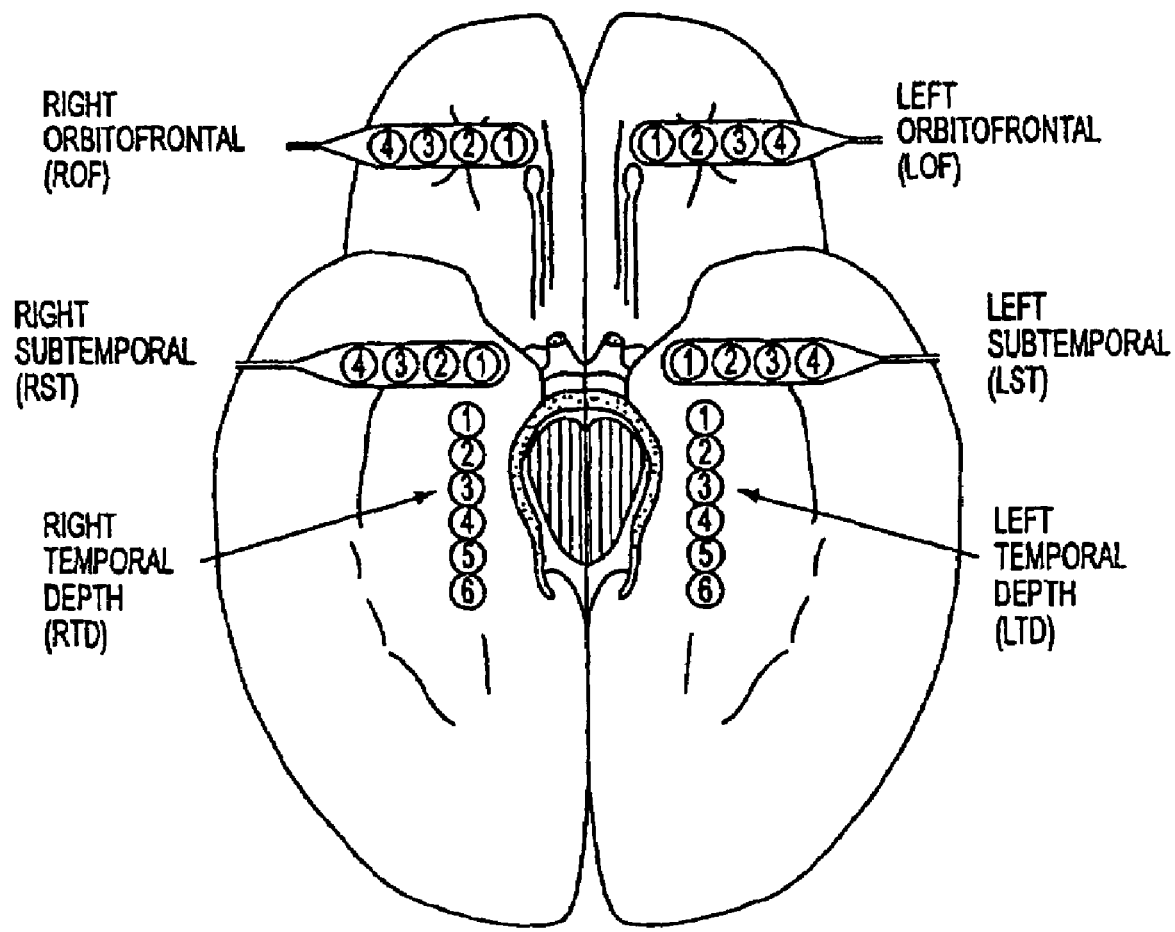
FIGS. 4A and 4B illustrate the placement and use of different electrodes and electrode configurations.
Figure 4B:
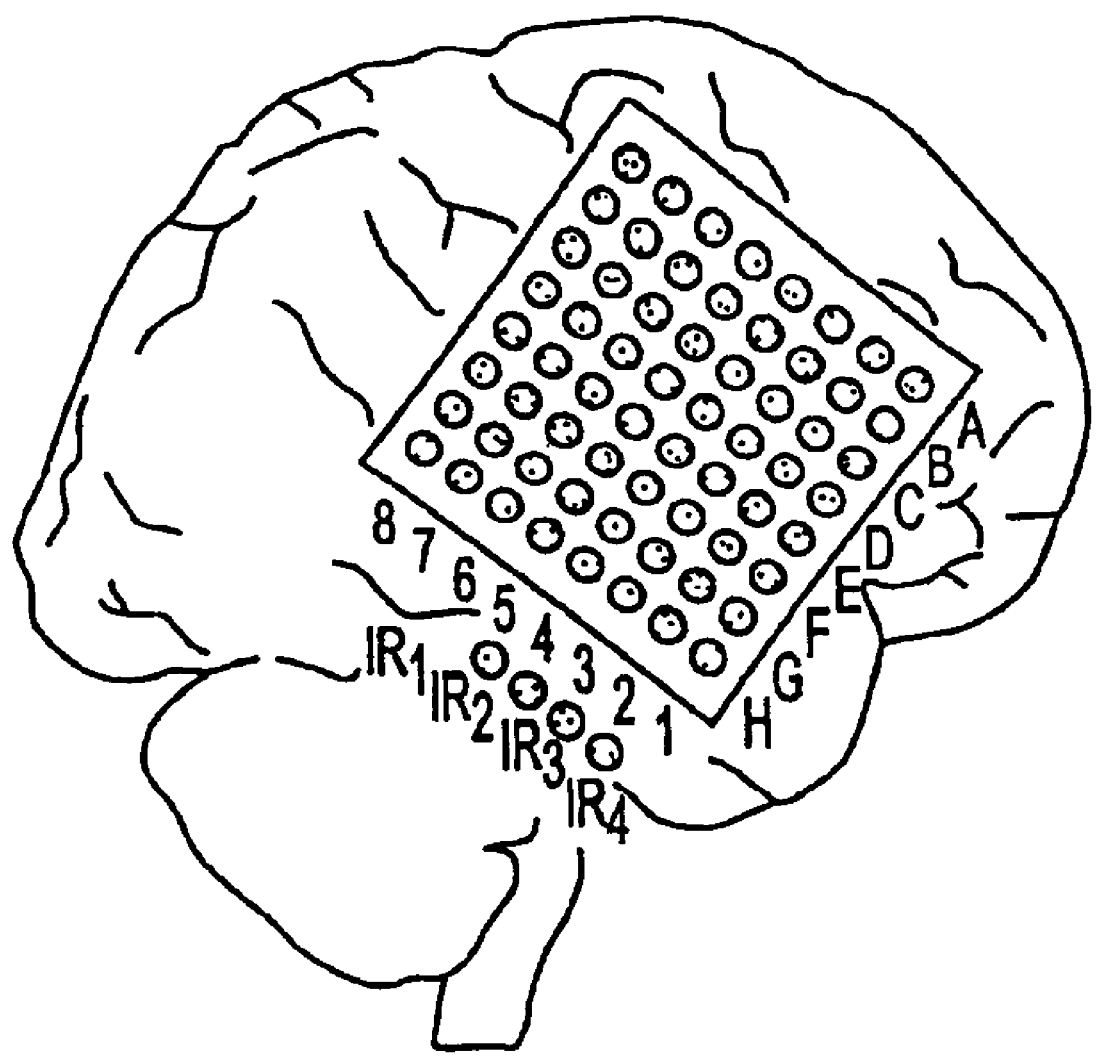

FIG. 4A provides a view from the inferior aspect of the brain and exemplary locations for a number of depth and subdural electrodes. As shown, the electrodes include six right temporal depth (RTD) electrodes and six left temporal depth (LTD) electrodes located along the anterior-posterior plane in the hippocampi. FIG. 4A also includes four right orbitofrontal (ROF), four left orbitofrontal (LOF), four right subtemporal (RST) and four left subtemporal (LST) subdural electrodes located beneath the orbitofrontal and subtemporal cortical surfaces. FIG. 4B illustrates the placement of and use of a subdural electrode array as well as a strip of electrodes on the inferior right temporal lobe.

In accordance with an alternative embodiment of the present invention, magneto-electroencephalography (MEG) may be employed to record the magnetic fields produced by the brain. With MEG, an array of sensors called superconducting quantum interference devices (SQUIDs) are used to detect and record the magnetic fields associated with the brain's internal current sources.

In yet another alternative embodiment, micro-electrodes may be implanted into the brain to measure the field potentials associated with one or just a few neurons. It will be understood that the use of micro-electrodes might be advantageous in very select applications, where, for example, it might be necessary to define with a high degree of accuracy the location of the epileptogenic focus prior to a surgical procedure.

Step 305 involves pre-processing the signals associated with each channel. Pre-processing includes, for example, signal amplification, filtering and digitization. In a preferred embodiment, filters, including a high pass filter with 0.1 to 1 Hz cutoff and a low pass filter with 70-200 Hz cutoff, are employed. Depending on the application and/or the recording environment, other filters may be employed. For instance, if the signals are being recorded in the vicinity of power lines or any electrical fixtures or appliances operating on a 60 Hz cycle, a 60 Hz notch filter or time varying digital filters may be employed. Pre-processing results in the generation of a digital time series for each channel. Each digital time series signal is then sampled per step 307.

Step 309 involves generating phase-space portraits, and in particular, p-dimensional phase-space portraits for each channel, where p represents the number of dimensions necessary to properly embed a brain state. It will be understood that the actual value of p may depend upon which dynamical parameters are being relied upon to measure the non-linear dynamical properties of each channel. For example, with regard to $STL_{MAX}$, it has been determined that p equal to seven (7) is adequate to capture the dynamic characteristics of the spatio-temporal response associated with a given channel. However, in the case of ApEn and PM-ApEn, a value of p equal to 2-3 maybe more appropriate.

In a preferred embodiment of the present invention, the p-dimensional phase-space portraits are generated as follows. First, the digital signals associated with each channel are sampled over non-overlapping or overlapping sequential time segments, referred to herein as epochs. Each epoch may range in duration from approximately 5 seconds to approximately 24 seconds, depending upon signal characteristics such as frequency content, amplitude, dynamic properties (e.g., chaoticity or complexity) and stationarity. Generally, epoch length increases as stationarity increases.

The samples associated with each signal, taken during a given epoch, are then used to construct a phase-space portrait for the corresponding channel. In a preferred embodiment of the present invention, the phase-space portraits are constructed using a method called "The Method of Delays." The Method of Delays is well known in the art. A detailed discussion of this method with respect to analyzing dynamic, nonlinear systems can be found, for example, in Iasemidis et al., "*Phase Space Topography of the Electrocorticogram and the Lyapunov Exponent in Partial Seizures*", Brain Topogr., vol. 2, pp. 187-201 (1990). In general, a phase space portrait is constructed using the Method of Delays by independently treating each unique sequence of p consecutive sample values, separated by a time delay, as a point to be plotted in the p-dimensional phase space. In an exemplary implementation of the present invention, equals 4 samples (20 msec).

Figure 5A:
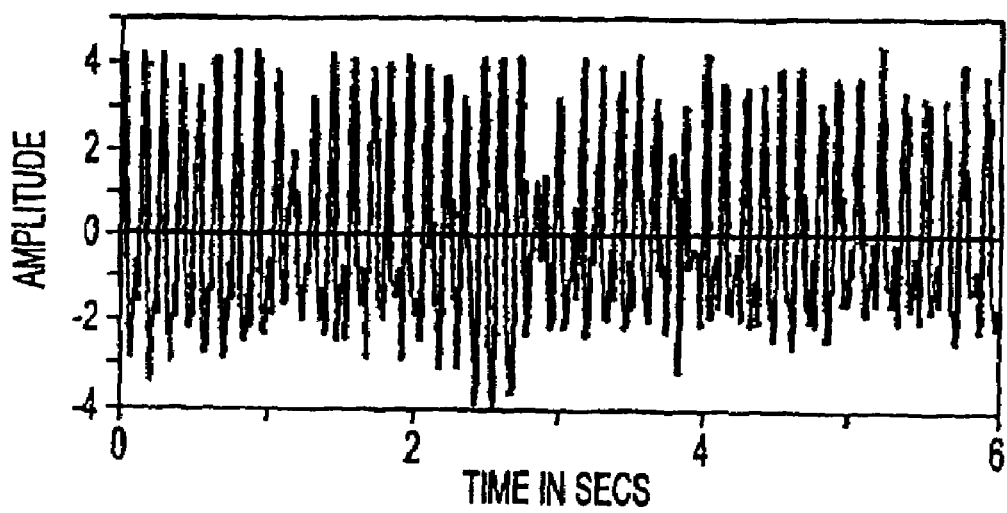
FIGS. 5A and 5B illustrate an EEG signal associated with a representative electrode channel over an epoch and the corresponding phase space portraits containing the attractor reconstructed from the EEG signal using the Method of Delays.
Figure 5B:
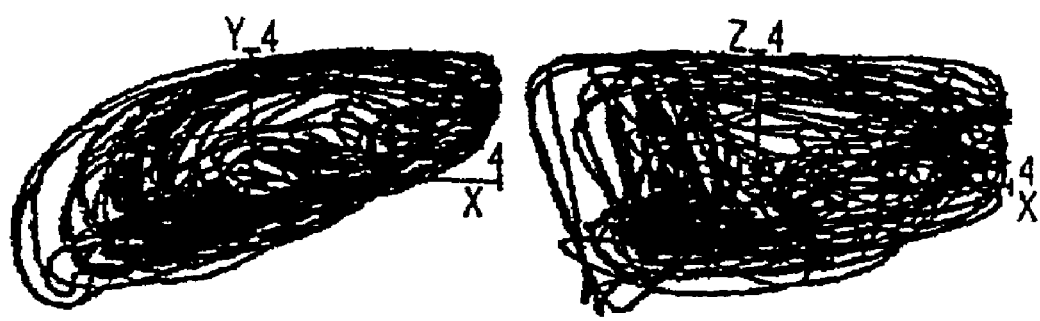

FIG. 5A shows a 6 second epoch associated with an exemplary EEG signal at the onset of a seizure that originated in the left temporal cortex. FIG. 5B illustrates, from different perspectives, the corresponding phase-space portrait, projected in three dimensions, for the exemplary EEG signal of FIG. 5A. The object appearing in the phase-space portrait of FIG. 5B is called an "attractor". The attractor represents the region within the phase-space in which the states of the system evolve and remain confined thereto until the structure of the system changes.

Step 311 involves quantifying the dynamical properties of the spatio-temporal responses of each channel, as embodied by an attractor(s) associated with each channel, in accordance with each of the multiple dynamical parameters: $STL_{MAX}$ (rate of divergence), $\Omega_{MAX}$ (rate of change in angular frequency), ApEn (approximate entropy or regularity statistic), PM-ApEn (pattern-match approximate entropy), $h_\mu$ (Pepsin's Identity) and $d_L$ (Lyapunov Dimension). Again, it will be understood that the list of dynamical parameters illustrated in FIG. 3 are exemplary, and not intended to be exhaustive.

As explained above, each dynamical profile represents the dynamical characteristics of a corresponding channel based on one of the multiple dynamical parameters, for example, $STL_{MAX}$, $\Omega_{MAX}$, ApEn, PM-ApEn, $h_\mu$ and $d_L$. Calculating the dynamical values associated with each of these exemplary dynamical parameters is now described herein below.

$L_{MAX}$ refers to the largest Lyapunov exponent. It is defined as the average of the local Lyapunov exponents $L_{ij}$ in the phase space where:

$$L_{\max} = \frac{1}{N_a} \cdot \sum_a L_{ij},$$

where $N_a$ is the total number of the local Lyapunov exponents estimated from the evolution of adjacent vectors in the phase space. $L_{ij}$ is defined by the follow equation:

$$L_{ij} = \frac{1}{\Delta} t \cdot \log_2 \frac{|X(t_i + \Delta t) - X(t_j + \Delta t)|}{|X(t_i) - X(t_j)|},$$

where $X_i = X(t_i)$ and $X_j = X(t_j)$, and where $\Delta t$ is the evolution time allowed for the vector difference $\delta_0(X_{ij}) = |X(t_i) - X(t_j)|$ to evolve to the new difference $\delta_k(X_{ij}) = |X(t_i + \Delta t) - X(t_j + \Delta t)|$, and where $\Delta t = k \cdot dt$ with dt being the sampling period of the data u(t). If $\Delta t$ is given in seconds, $L_{MAX}$ is in bits/sec. $STL_{MAX}$ is the short-term Lyapunov exponent. A method for computing $STL_{MAX}$ is described in Iasemidis et al., "*Phase Space Topography of the Electrocorticogram and the Lyapunov Exponent in Partial Seizures*," Brain Topography, vol. 2, no. 3, pp. 187-201 (1990).

The difference in phase ($\Delta\Phi$) in the phase space is defined as the average of the local differences $\Delta\Phi_i$ as given by the following equation:

$$\Delta\Phi = \frac{1}{N_a} \cdot \sum_{i=1}^{N_a} \Delta\Phi_i,$$

where $N_a$ is the total number of phase differences estimated from the evolution of $X(t_i)$ to $X(t_i + \Delta t)$ in the phase space, and where $\Delta\Phi_i$ is given by the following equation.

$$\Delta\Phi_i = \left|\arccos\left(\frac{X(t_i) \cdot X(t_i + \Delta t)}{\|X(t_i)\| \cdot \|X(t_i + \Delta t)\|}\right)\right|.$$

The rate of angular frequency change ($\Omega_{MAX}$) is then given by the following equation.

$$\Omega_{\max} = \frac{1}{\Delta t}\Delta\Phi$$

If $\Delta t$ is given in seconds, then $\Omega_{MAX}$ is in radians/second. Further information regarding the computation of $\Omega_{MAX}$ may be found, for example, in Iasemidis et al., "*Prediction of Human Epileptic Seizures Based on Optimization and Phase Changes of Brain Electrical Activity*," Optimization Methods and Software, 18 (1):81-104 (2003).

Entropy has been shown to be a critical "summary" statistic in nonlinear dynamical system analysis and chaos. Approximate Entropy (ApEn) measures the regularity of an observed time series data signal. See Pincus, "*Approximate Entropy as a Measure of System Complexity*," Proceedings of the National Academy of Science of the United States of America, vol. 88 pp. 2297-2301 (1991). It has been widely used in distinguishing normal and abnormal medical time series data (e.g., heart rate and electrocardiogram data). ApEn may be calculated in accordance with the following process:

(a) given a time series data signal $U=\{u_1, u_2, \ldots, u_n\}$, where each entry is equally spaced in time;
(b) fix an integer l; where $x_i = \{u_i, u_{i+1}, \ldots, u_{i+l-1}\}$;
(c) form a sequence of vectors $x_1, x_2, \ldots, x_{n-l+1}$ in $R^l$;
(d) for a given positive real number r, use the sequence $x_1, x_2, \ldots, x_{n-l+1}$ to construct, for each i, $1 \leq i \leq n-l+1$, where, the following:

$$C_i^l(r) = \frac{\text{number of } x_j\text{'s such that } d(x_i, x_j) \leq r}{n - l + 1}, \text{ where}$$

$$d(x_i, x_j) = \max_{0 \leq k \leq l-1} |u_{i+k} - u_{j+k}|, \text{ i.e.,}$$

$d(x_i, x_j)$ represents the maximum distance between vectors $x_i$ and $x_j$ in their respective scalar components;

(e) define the following:

$$\Phi^l(r) = \sum_{i=1}^{n-l+1} \ln C_i^l(r)/(n-l+1)$$

(f) then Approximate Entropy ApEn is defined in accordance with the following equation:

$$-ApEn = \Phi^l(r) - \Phi^{l+1}(r)$$

(g) where it is noted that:

$$-ApEn = \Phi^l(r) - \Phi^l(r) \approx \frac{1}{n-l}\sum_{i=1}^{n-l}\ln\frac{C_i^{l+1}(r)}{C_i^l(r)},$$

and where:

$$\frac{C_i^{l+1}(r)}{C_i^l(r)} = \frac{Pr(|u_{j+k} - u_{i+k}| \leq r, k = 0, 1, \ldots, l)}{Pr|u_{j+k} - u_{i+k}| \leq r, k = 0, 1, \ldots, l-1)}$$

which in turn equals:

$$Pr(|u_{j+l} - u_{i+l}| \leq r||u_{j+k} - u^{i+k}| \leq r, k = 0 \sim l-1)$$

Given the algorithm described above for calculating ApEn, it is noted that the calculation of ApEn is based on the following conditional probability.

Pr(next point value matched|the previous l points all value matched)

Because value match criterion is very sensitive to the matching critical value r, ApEn gives inconsistent results for different choices of parameters l and r. Accordingly, PM-ApEn can be derived as follows:

(a) given a time series data signal $U=\{u_1, u_2, \ldots, u_n\}$, where $\delta_u$ is the sample standard deviation of U, and where, for a fixed integer l, a subsequence of U is defined as follows:

$$x_i = \{u_i, u_{i+1}, \ldots, u_{i+l-1}\}$$

where $$1 \leq i \leq n-1+l;$$

(b) for a given positive real number r (e.g., $r=0.2\delta_u$), $x_i$ and $x_j$ are considered pattern l-matched to each other if the following is true:

$$|u_i - u_j| \leq r;$$

$$|u_{i+l-1} - u_{j+l-1}| \leq r;$$

and $$\text{sign}(u_{i+k} - u_{i+k-1}) = \text{sign}(u_{j+k} - u^{j+k-1}), \text{ where } k=1, \ldots, l-1$$

(c) then, Pattern-Match ApEn is defined by an equation similar to the equation for ApEn, but change value match to pattern match, where:

$$p_i = Pr\{\text{sign}(u_{i+1} - u_{i+l-1}) = \text{sign}(u_{j+l} - u_{j+1l-1})|\text{previous l points are pattern l-match}\}$$

(d) the Pattern-Match ApEn can then be written as follows:

$$PM - ApEn = -\frac{1}{n-1}\sum_{i=1}^{m-l}\ln\hat{p}_i$$

where it should be noted that when the time series is more regular, the PM-ApEn should be smaller.

Lyapunov exponents may be used to define the metric entropy of EEG signals through Pesin's theorem. The Lyapunov spectrum (i.e., all Lyapunov exponents) and the metric entropy are related by Pesin's Identity, which may be defined as follows:

$$h_\mu = \sum_{i=1}^{r} \text{positive } \lambda_i,$$

where $\lambda_i$ represents the $i^{th}$ Lyapunov exponent and r represents the maximum number of positive Lyapunov exponents.

The Lyapunov dimension is a characteristic related to the Lyapunov spectrum and the predictability of EEG signals. The state-space hypersurface of dimension m of the EEG signals expands at a rate governed by the sum of all Lyapunov exponents. Thus, Lyapunov Dimension may be defined in accordance with the following equation:

$$d_L = k + \frac{\sum_{i=1}^{k} \lambda_i}{|\lambda_{k+1}|},$$

where k represents the largest number such that $$\sum_{i=1}^{k} \lambda_i > 0,$$

and the second term characterizes the fractional part of the dimension. It may be anticipated that, for an epileptic attractor, the Lyapunov dimension is equal to the information dimension.

Figure 6:
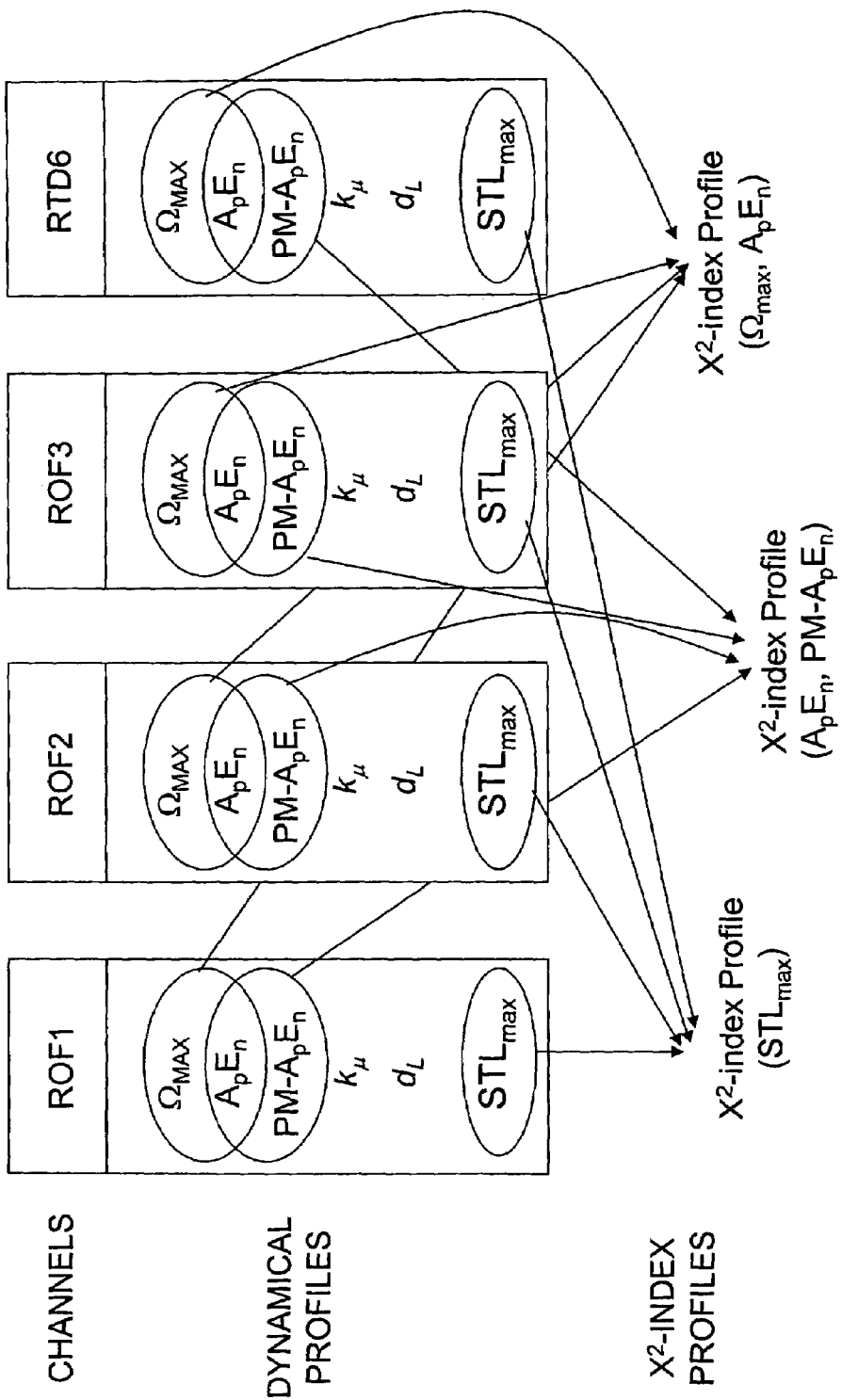
FIG. 6 depicts the process of generating chaoticity profiles associated with each of multiple chaoticity parameters, for one or more channels, and therefrom, generating statistical profiles for one or more channel pairs.

In accordance with a preferred embodiment, step 311, as stated, further involves generating several $X^2$-index profiles for at least one channel group, where each $X^2$-index profile is based on corresponding dynamical profiles associated with one or a combination of dynamical parameters. This is illustrated in FIG. 6, where the algorithm is shown to have generated $X^2$-index profiles for the exemplary channel group: ROF1-ROF2-ROF3-RTD6. It will be understood, however, the algorithm may generate additional $X^2$-index profiles based on the dynamical profiles of other dynamical parameters or combinations thereof. Moreover, it will be understood that $X^2$-index profiles may generated by the algorithm for additional channel groups.

Figure 7:
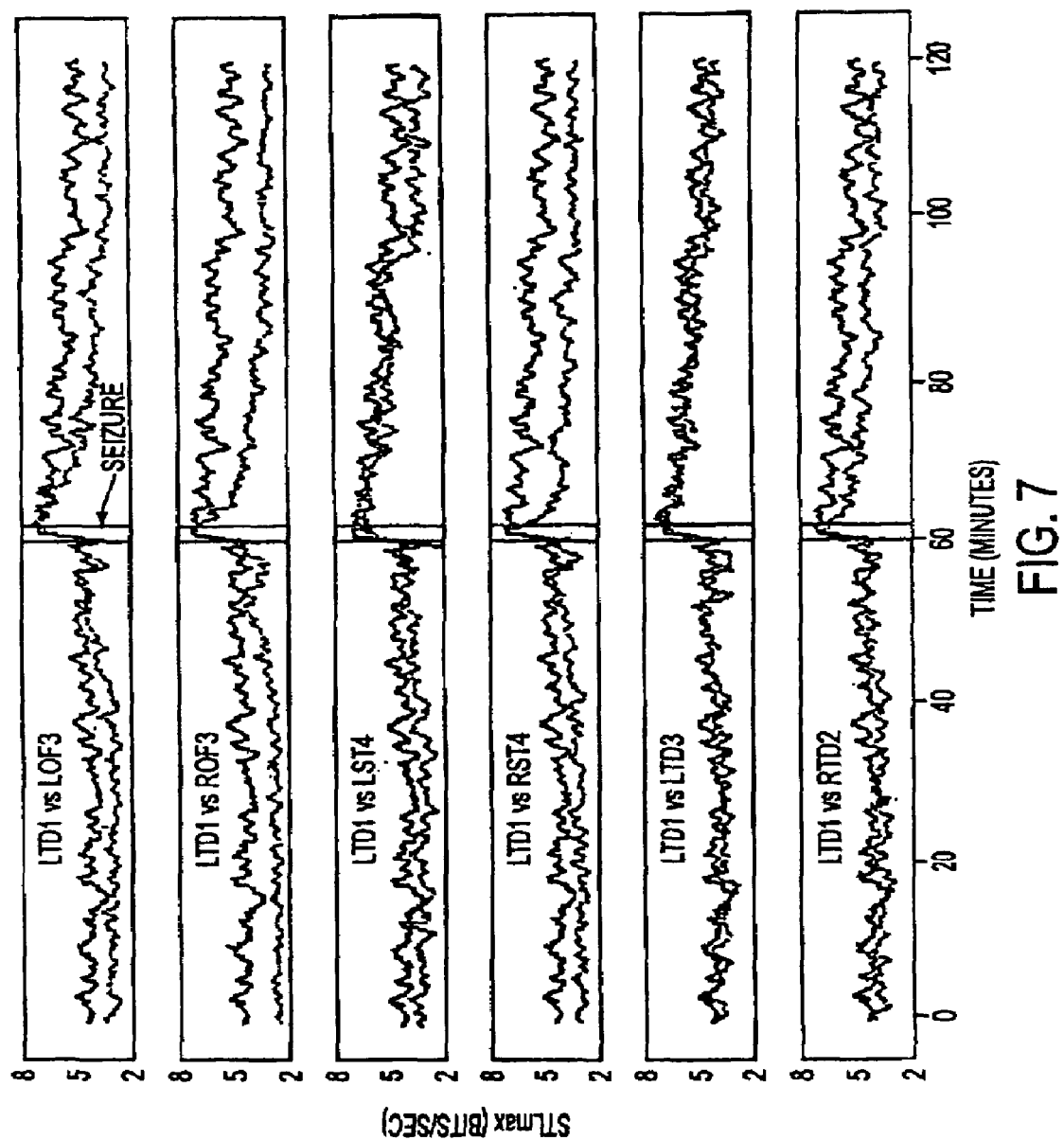
FIG. 7 illustrates the $L_{MAX}$ profiles associated with each of a representative number of channel pairs.

The nonparametric randomized block ANOVA test is well known in the art. Generally, the algorithm applies this test to generate the $X^2$-index profiles by comparing the dynamical profiles associated with a corresponding one or more dynamical parameters. For example, the algorithm generates the $X^2$-index profile relating to $\Omega_{MAX}$ and ApEn, as illustrated in FIG. 6, by comparing the dynamical profiles associated with $\Omega_{MAX}$ and ApEn for each channel of the channel group (e.g., the channel group ROF1-ROF2-ROF3-RTD6). If, at the end of the initialization period, $\Omega_{MAX}$ and ApEn are selected in accordance with method step 317, the X2-index profile thereafter generated by the algorithm based on the dynamical profiles associated with $\Omega_{MAX}$ and ApEn, for at least one channel group (e.g., the channel group ROF1-ROF2-ROF3-RTD6), is used to determine whether the spatio-temporal responses associated with the channels that make up the at least one channel group show signs of entrainment. For the purpose of the present invention, the term "entrain" refers to a correlation or convergence in amplitude and/or phase among the channels that make up the channel group. FIG. 7 illustrates, for example, a comparison of the dynamical profiles associated with the dynamical parameter $STL_{MAX}$, for each of a representative number of channel groups comprising two channels each.

Figure 8:
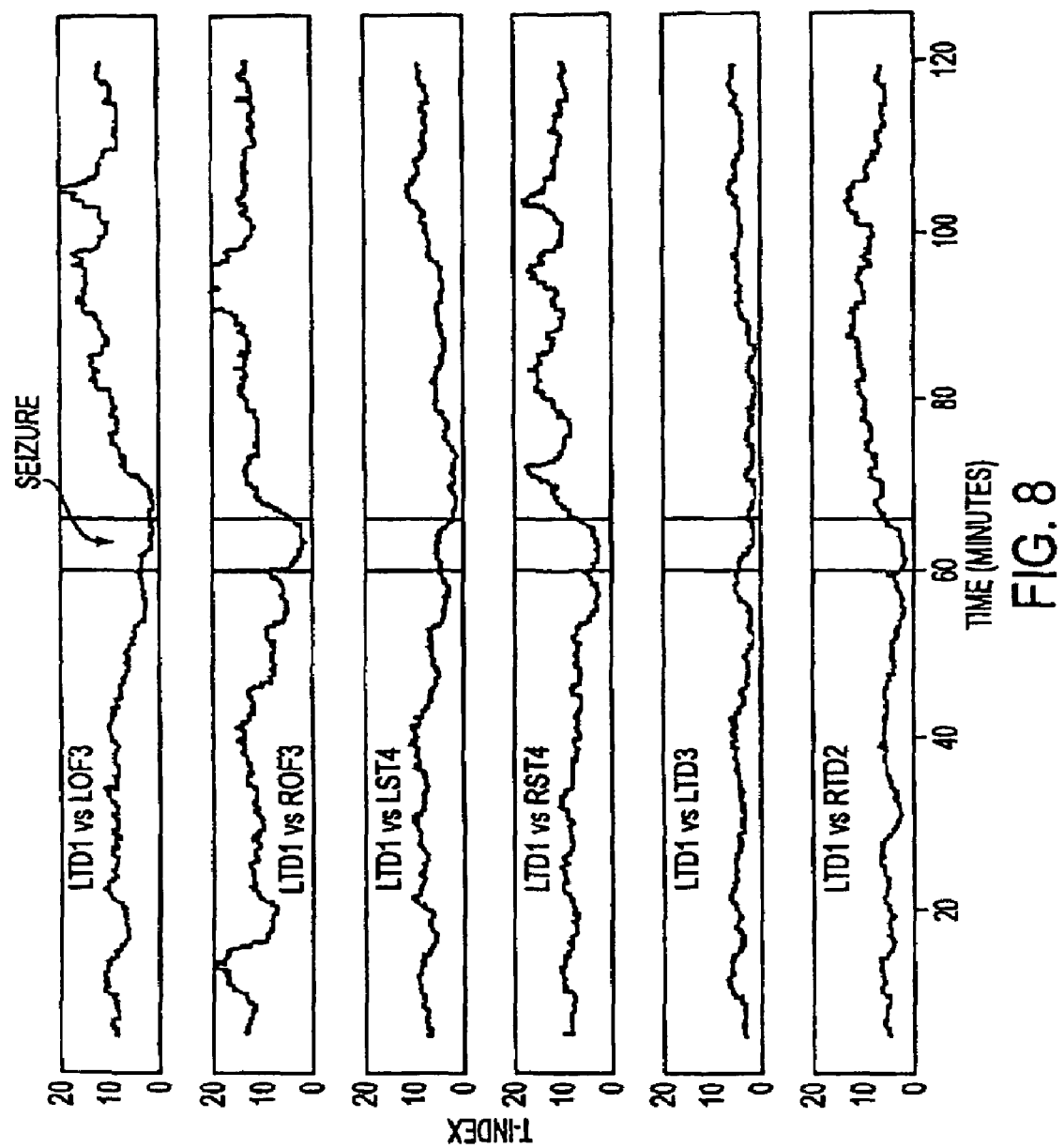
FIG. 8 illustrates a procedure for comparing $L_{MAX}$ profiles (e.g., estimations of T-index profiles) for the representative number of channel pairs shown in FIG. 7.

FIG. 8 illustrates statistical profiles, in this instance T-index profiles, for the six channel groups shown in FIG. 7. In FIG. 8, the statistical profiles are, as stated, T-index profiles, as they are generated by the algorithm based on a signal dynamical parameter, $STL_{MAX}$, for channel groups comprising only two channels (i.e., channel pairs). From the T-index profiles illustrated in FIG. 8, it is evident that the $STL_{MAX}$ profiles associated with each channel pair all progressively become entrained during the preictal stage (i.e., during the 0-60 minute time frame), while each channel pair becomes progressively disentrained during the postictal stage. However, the rate and degree at which the $STL_{MAX}$ profiles become entrained and disentrained vary. In FIG. 8, the channel pair associated with the electrode LTD1 and electrode LTD3 demonstrates a relatively high level of entrainment (i.e., relatively low T-index values), more so than the other five channel pairs. The channel pair associated with the electrode LTD1 and electrode RTD2 also shows a relatively high level of entrainment, particularly during the preictal stage. Although FIG. 8 only shows T-index values 60 minutes prior to and 60 minutes following seizure onset, the preictal period typically begins approximately 15 minutes to as much as 2 hours prior to seizure onset. However, it is extremely important to note that signs of entrainment, such as reduced T-index values may be evident long before seizure onset. In fact, it is possible that some channels will exhibit signs of an impending seizure days before an actual seizure. Again, it is noted that while FIG. 8 illustrates the entrainment of $STL_{MAX}$ dynamical profiles, by application of a T-statistic, the present invention may rely on dynamical profiles associated with multiple dynamical parameters, thus generating $X^2$-index profiles, which may prove to be better indicators of impending seizures than $STL_{MAX}$ alone.

Step 323 involves generating an ISW, SSPD and/or a TISP. The specific techniques employed to generate an ISW, SSPD and/or TISP, in accordance with this step, will now be described in greater detail. The first of these features to be described is the ISW feature. In accordance with the method of FIG. 3, an ISW is triggered when the $X^2$-index values associated with the at least one channel group become highly disentrained (e.g., the $X^2$-index value exceeds $X^2_D$) followed by the $X^2$-index values becoming highly entrained (e.g., the $X^2$-index value falls below $X^2_E$) for a statistically significant period of time. Further in accordance with a preferred embodiment, the statistically significant period of time during which the $X^2$-index value must remain below $X^2_E$ in order to trigger an ISW is typically set somewhere between 0 minutes and 1.5 hours. For example, an average $X^2$-index value less than $X^2_E$ for a period of time equal to 15 minutes equates to a 99 percent confidence level that the issuance of an ISW is a valid warning. Of course, it will be understood that the threshold value $X^2_E$ and the duration which the $X^2$-index must remain below that threshold value may be adaptively adjusted to increase or decrease ISW sensitivity and reduce the incidence of false warnings (i.e., false positives) for any given patient, or reduce the incidence of failed warnings (i.e., false negatives).

The ISW may be implemented in any number of ways. For example, the ISW may involve audible warnings or visual warnings or a combination of both visual and audible warnings. In fact, the ISW may involve nothing more than the setting or resetting of an internal software variable or flag, wherein the setting or resetting of the variable or flag triggers a dependent event, such as the automatic delivery of anti-seizure medication. Accordingly, the specific implementation of the ISW will depend on the specific clinical or non-clinical application for which the present invention is being employed.

Figure 9:
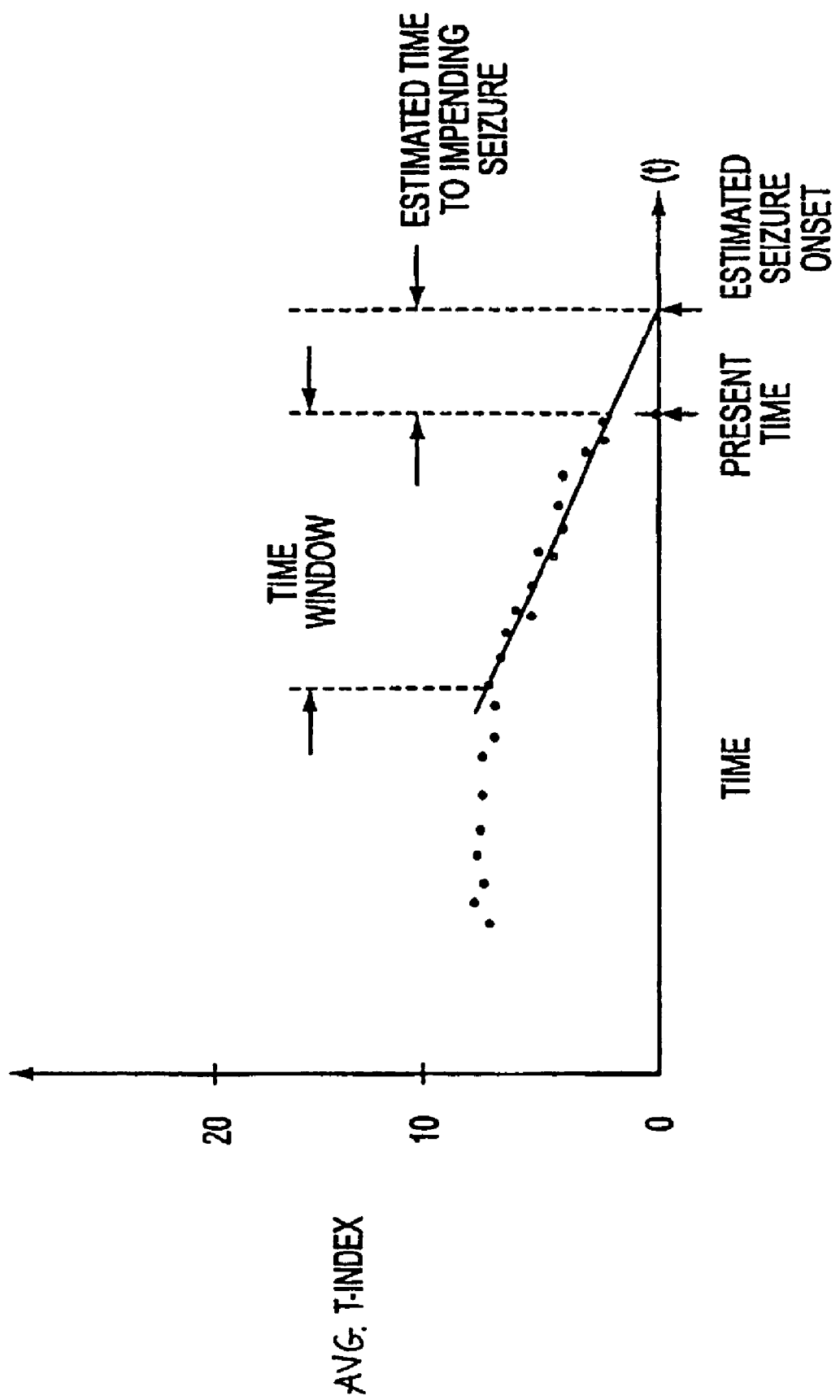
FIG. 9 illustrates the TISP feature in accordance with exemplary embodiments of the present invention.
Figure 1O:
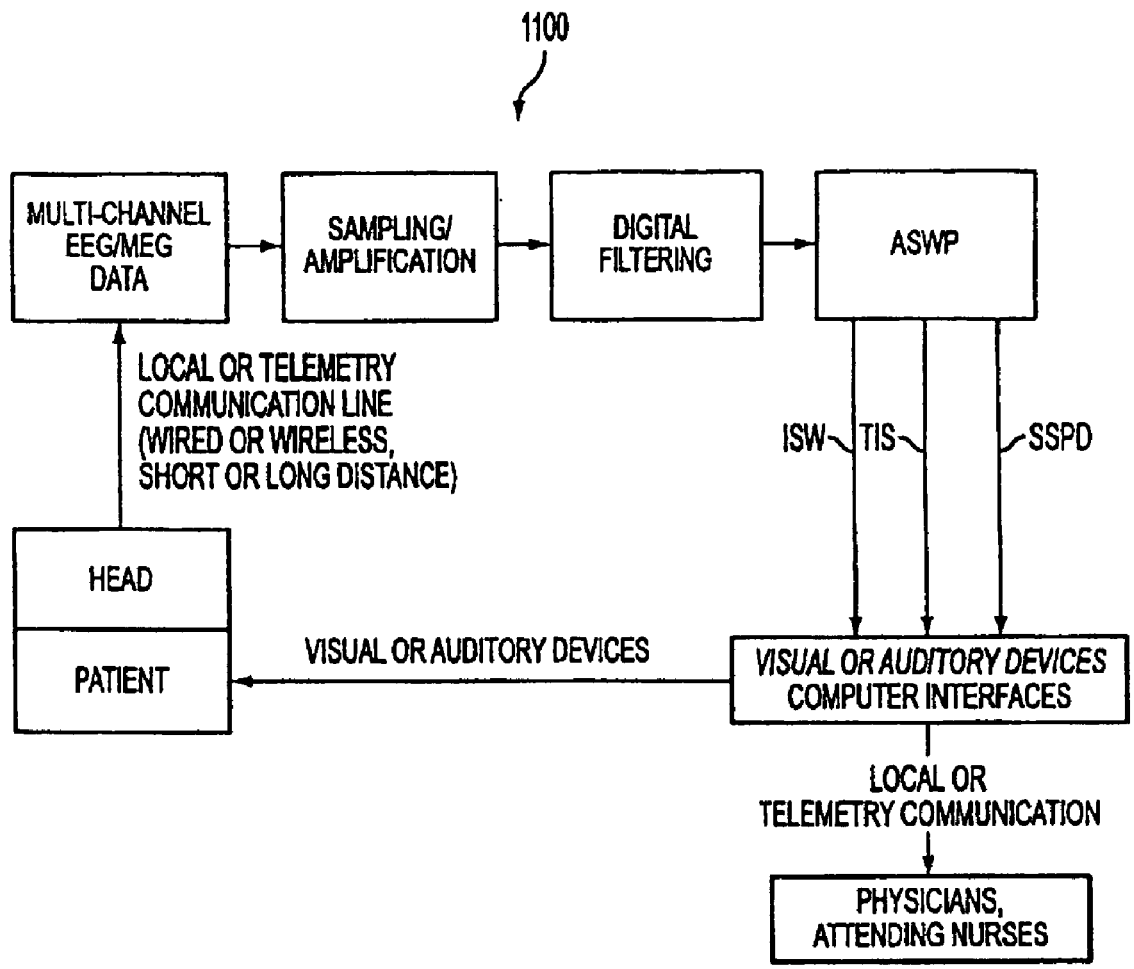

The next feature is the TISP feature. Once the algorithm generates an ISW, the rate of entrainment, that is, the rate at which the dynamical profiles associated with the selected one or combination of dynamical parameters, for the at least one channel group, continue to converge may be used to estimate the amount of time before seizure onset. In accordance with a preferred embodiment of the present invention, this is accomplished by continuously deriving, for the at least one channel group, the slope of the corresponding $X^2$-index profile over a "sliding" time window, as illustrated in FIG. 9. The point at which the slope intercepts the time (t) axis represents an estimated seizure onset time. Therefore, the difference between the present time and the estimated seizure onset time, along the time (t) axis, represents the TISP. The length of the "sliding" time window may, once again, vary. Initially, it may be set to a relatively small time interval (e.g., 15 minutes). Thereafter, it may be adaptively optimized for each individual patient.

The last of the three features is the SSPD feature. Over a period of several hours, if not several days prior to a seizure, or a first of a series of seizures, there is generally a gradual entrainment among certain critical sites. The concept of critical sites, critical channel pairs and critical channel groups is more fully set forth in U.S. Pat. No. 6,304,775 and co-pending U.S. patent application Ser. No. 10/648,354. The present invention exploits this to provide the SSPD feature. Specifically, the SSPD feature is, in accordance with a preferred embodiment of the present invention, implemented in much the same way as the ISW feature, that is, by generating an $X^2$-index profile, based on the selected one or combination of dynamical parameters, for each of the at least one channel groups, and by observing the levels of entrainment associated with those $X^2$-index profiles. The $X^2$-index profiles may be generated and observed over a period of several hours or days, rather than minutes.

As one skilled in the art will readily appreciate, the aforementioned methods will be implemented as an integral component of a larger system. FIG. 10 is a block diagram of an exemplary system. This and other such exemplary systems are fully described in U.S. Pat. No. 6,304,775 and co-pending U.S. patent application Ser. No. 10/648,354. These systems may be employed for diagnostics, patient treatment, seizure intervention and, potentially, many other clinical and non-clinical applications.

The present invention has been described with reference to a number of exemplary embodiments. However, it will be apparent to those skilled in the art that it is possible to embody the invention in specific forms other than those described above without departing from the spirit of the invention. In fact, it will be readily apparent that the present invention may be employed for other medical (e.g., heart pacemakers, stroke diagnosis and prevention, dynamic brain disorders, etc . . . ), non-medical, non-linear, multi-dimensional dynamic processes characterized by sudden phase transitions. Accordingly, the various embodiments described above are illustrative, and they should not be considered restrictive in any way. The scope of the invention is given by the appended claims, rather than the preceding description, and all variations and equivalents thereof that fall within the range of the claims are intended to be embraced therein.

What is claimed is:

1. A computer-implemented method of analyzing a multi-dimensional system comprising the steps of:
   generating a multi-dimensional signal for each of a plurality of channels associated with the multi-dimensional system;
   generating multiple dynamical profiles for each channel based on the corresponding multi-dimensional signal, where each profile reflects the dynamical characteristics of the corresponding channel in accordance with one of multiple dynamical parameters;
   for a group of channels, generating a number of statistical measures, wherein each of the statistical measures reflects a correlation level between corresponding dynamical profiles, and wherein each of the corresponding dynamical profiles is associated with one of the multiple dynamical parameters;
   selecting at least one dynamical parameter from amongst the multiple dynamical parameters;
   generating a statistical measure for the channel group, wherein the statistical measure reflects a correlation level between corresponding dynamical profiles associated with the selected at least one dynamical parameter;
   characterizing the behavior of the multi-dimensional system as a function of the statistical measure, generated for the channel group, that reflects the correlation level between corresponding dynamical profiles associated with the selected at least one dynamical parameter; and
   outputting a signal indicative of the characterization of the behavior of the multi-dimensional system.

2. The method of claim 1, wherein said step of selecting at least one dynamical parameter from amongst the multiple dynamical parameters comprises the step of:
   selecting a combination of dynamical parameters.

3. The method of claim 2, wherein the combination of dynamical parameters corresponds with one of the statistical measures generated for the channel group.

4. The method of claim 2, where in the statistical measure corresponding to the selected combination of dynamical parameters was determined to characterize the behavior of the multidimensional system better than the other statistical measures generated for the channel group.

5. The method of claim 1, wherein each of the statistical measures generated for the channel group are a function of corresponding dynamical profiles associated with one or a combination of dynamical parameters.

* * * * *

UNITED STATES PATENT AND TRADEMARK OFFICE
CERTIFICATE OF CORRECTION

| | |
|---|---|
| PATENT NO. | : 7,263,467 B2 |
| APPLICATION NO. | : 10/673329 |
| DATED | : August 28, 2007 |
| INVENTOR(S) | : James Chris Sackellares et al. |

It is certified that error appears in the above-identified patent and that said Letters Patent is hereby corrected as shown below:

Col. 1, lines 18-23;

Page 1 of the Description, replace paragraph 2 with the following paragraph, entitled:

STATEMENT REGARDING FEDERALLY SPONSORED
RESEARCH AND DEVEOPMENT

This invention was made with government support under grant number NS039687 awarded by National Institutes of Health. The government has certain rights in the invention.

Signed and Sealed this

Twenty-ninth Day of April, 2008

JON W. DUDAS
*Director of the United States Patent and Trademark Office*